United States Patent [19]

Nakamura et al.

[11] Patent Number: 5,469,852
[45] Date of Patent: Nov. 28, 1995

[54] ULTRASOUND DIAGNOSIS APPARATUS AND PROBE THEREFOR

[75] Inventors: Hisashi Nakamura; Yasutaka Nagai; Susumu Hiki, all of Tokyo, Japan

[73] Assignee: Kabushiki Kaisha Toshiba, Kawasaki, Japan

[21] Appl. No.: 209,215

[22] Filed: Mar. 11, 1994

[30] Foreign Application Priority Data

| Mar. 12, 1993 | [JP] | Japan | 5-052403 |
| Mar. 12, 1993 | [JP] | Japan | 5-052405 |
| Mar. 12, 1993 | [JP] | Japan | 5-052689 |
| Mar. 18, 1993 | [JP] | Japan | 5-058884 |

[51] Int. Cl.⁶ ................................. A61B 8/12
[52] U.S. Cl. ................................. 128/662.06
[58] Field of Search ............. 128/660.08, 660.09, 128/660.10, 662.03, 662.06

[56] References Cited

U.S. PATENT DOCUMENTS

| 4,543,960 | 10/1985 | Harui et al. |            |
| 4,880,011 | 11/1989 | Imade et al. | 128/662.06 |
| 5,054,492 | 10/1991 | Scribner et al. | 128/662.06 |
| 5,099,850 | 3/1992  | Matsui et al. | 128/662.06 |
| 5,181,514 | 1/1993  | Solomon et al. |            |
| 5,186,176 | 2/1993  | Hiki et al. |            |
| 5,207,225 | 5/1993  | Oaks et al. |            |
| 5,257,628 | 11/1993 | Ishiguro et al. | 128/662.06 |

FOREIGN PATENT DOCUMENTS

| 0509297   | 10/1992 | European Pat. Off. |
| 0509296   | 10/1992 | European Pat. Off. |
| 59-22534  | 2/1984  | Japan |
| 2-206450  | 8/1990  | Japan |
| 4-282141  | 10/1992 | Japan |
| 5-154152  | 6/1993  | Japan |
| 5-161648  | 6/1993  | Japan |
| 5-161649  | 6/1993  | Japan |
| 5-161653  | 6/1993  | Japan |
| 5-51313   | 7/1993  | Japan |
| WO92/02178 | 2/1992 | WIPO |
| WO92/02179 | 2/1992 | WIPO |
| WO92/02180 | 2/1992 | WIPO |

*Primary Examiner*—George Manuel
*Attorney, Agent, or Firm*—Oblon, Spivak, McClelland, Maier, & Neustadt

[57] ABSTRACT

An ultrasound diagnostic apparatus and a probe therefor for a body cavity of a patient are disclosed. The probe comprises a transducer which rotates to obtain sectional ultrasound images along various angles. The apparatus comprises a means for indicating the rotation angle of the transducer. A mark for indicating the angle is provided on a surface of the transducer. The rotation angle is detected electrically to be displayed on a CRT screen. For more precise detection, slack removers for removing slacks of rotation wires are provided. A rotation angle indicator for indicating the rotation angle of a rotation knob which represents the rotation angle of the transducer is provided on the operation portion.

55 Claims, 16 Drawing Sheets

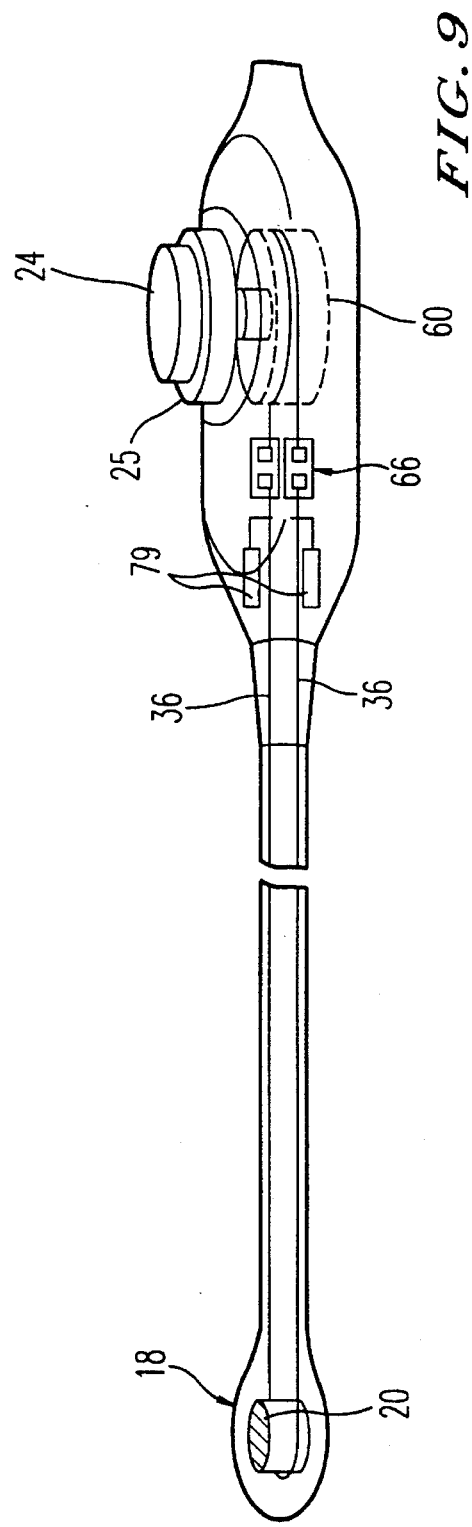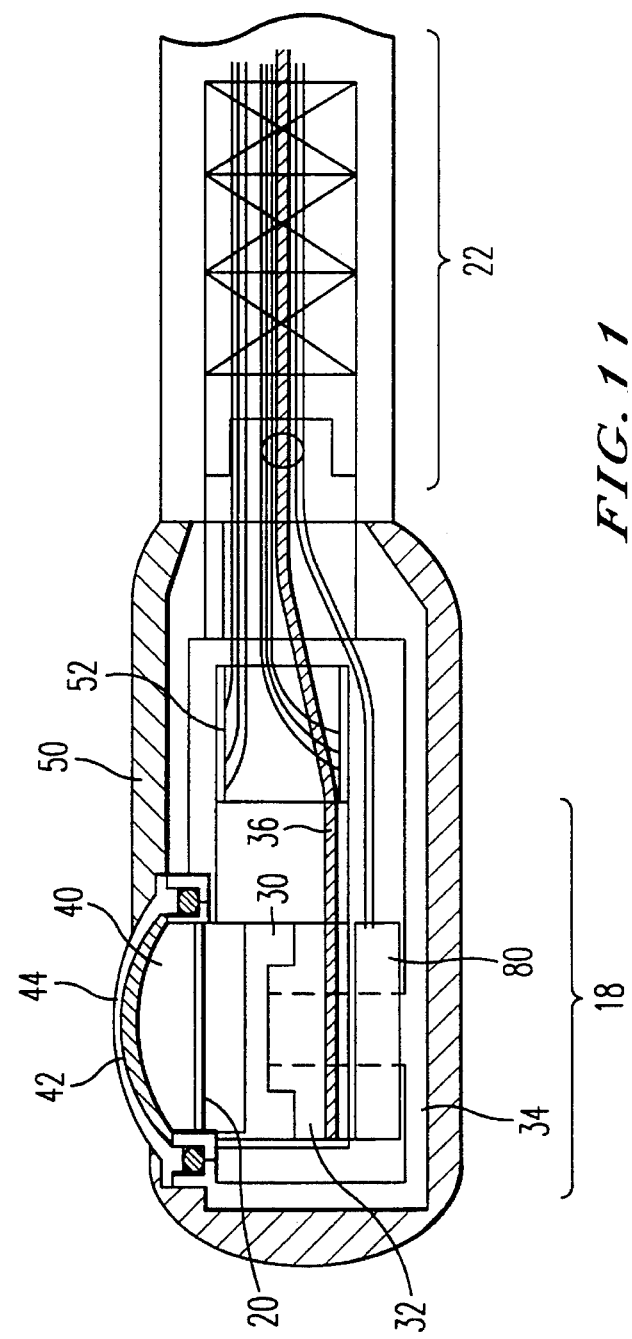

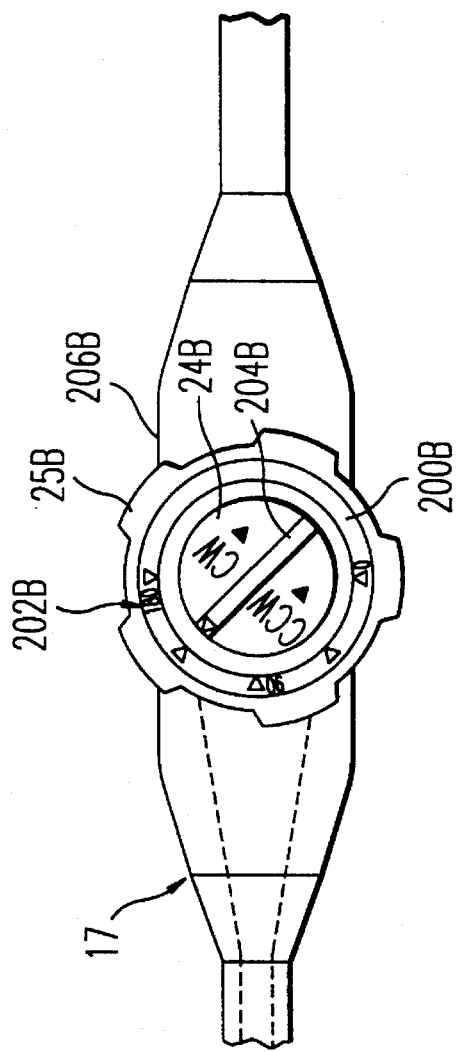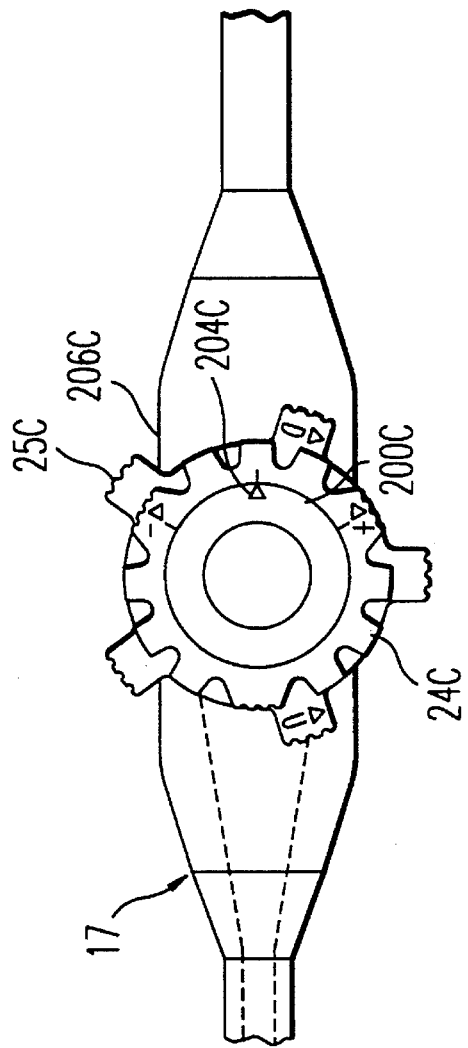
FIG. 19A
FIG. 19B

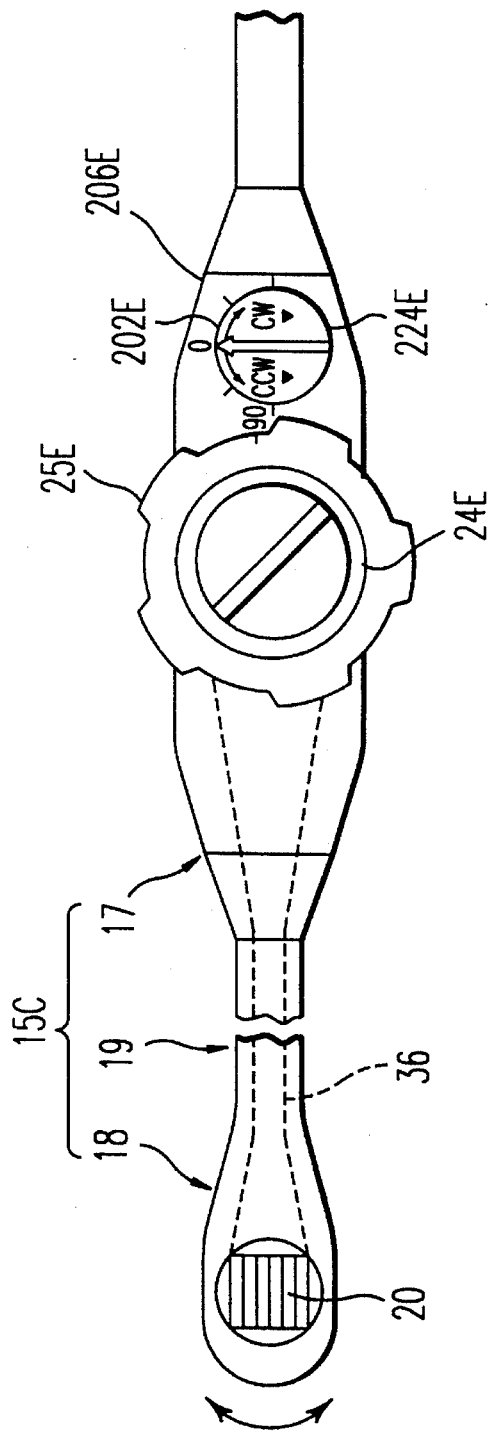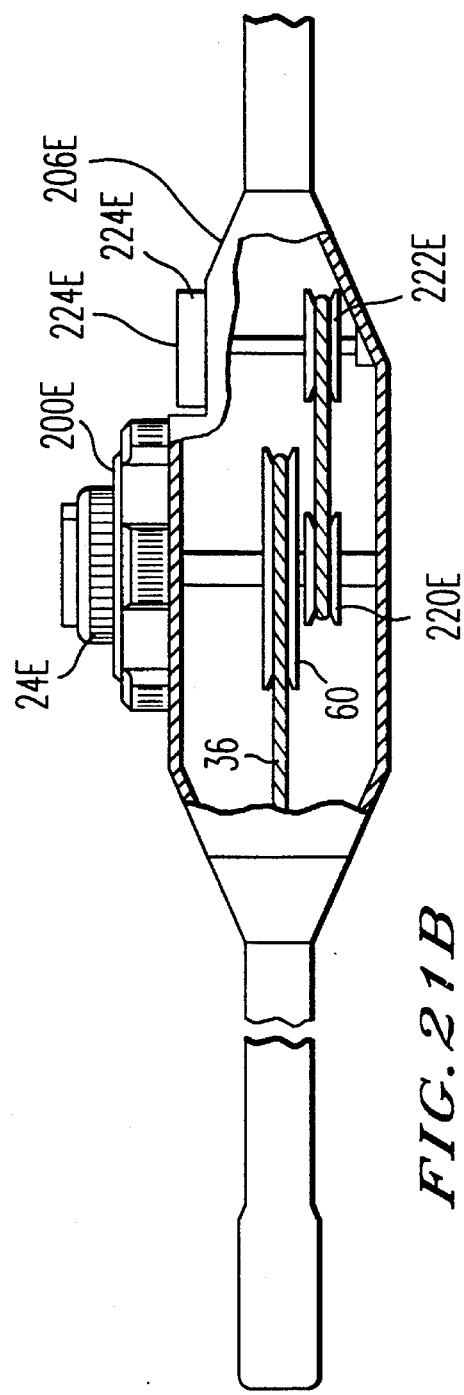
FIG. 21A
FIG. 21B

ULTRASOUND DIAGNOSIS APPARATUS AND PROBE THEREFOR

BACKGROUND OF THE INVENTION

This invention relates to an ultrasound diagnosis apparatus and a probe therefor. More specifically, this invention relates to an ultrasound apparatus utilizing a multi-plane ultrasound probe to be inserted into a body cavity, such as an esophagus, of a patient for obtaining ultrasound cross-sectional images along various angles.

As an example of an ultrasound probe of this type, there has been utilized a multi-plane TEE (transesophageal echocardiography) probe for being inserted transesophageally into an upper digestive tract, such as an esophagus or a stomach, of the patient and for obtaining cross-sectional images of a heart of the patient. Japanese laid-open (Kokai) patent 59-22534 discloses an ultrasound probe of this type. This probe comprises an array of ultrasound transducer elements on the end or side of a probe head and obtains cross-sectional images from the inside of the body cavity. The transducer elements are driven sequentially along one direction. The array can be rotated about an axis extending through the center of the array and perpendicular to its surface. This mechanism allows to obtain ultrasound cross-sectional images along various angles without moving the probe head in the body cavity. Imaging at any desirable angles is possible not being interfered by bones or subcutaneous fat layers.

The above-mentioned Japanese Kokai patent, U.S. Pat. No. 4,543,960 and European laid-open patent No. 509296 disclose unique mechanisms for rotation of the transducer array. The former two disclose wires to for rotation and the latter a shaft and a worm gear system.

As described above, the conventional multi-plane probe has a transducer array which is mechanically rotatable by manual operation to obtain cross-sectional images along various angles. However, the rotation wire may extend after a long use and this may cause inaccurate power transmission from an operation part to the array. Further, the wire operation for the rotation of the array may cause an undesired motion of an angle portion which varies a direction of the probe head. When the angle portion of the probe is bent, the power transmission by the wire may not be accurate because of the difference between the lengths of the inner and outer wires. Therefore, in the conventional multi-plane probe, the rotation angle may not be set accurately and the response of the rotation may not be sufficient. Generally, since the probe of this type is stuck to the inner wall of the esophagus and may cause pain to the patient, examination time is desired to be short and the poor response and inaccuracy is not favorable. Even in the shaft mechanism, developed to solve this problem, twisting of the shaft which is caused by low rigidity to keep flexibility may cause the same problems. In addition, backlash of the gear may cause the inaccuracy.

Furthermore, when rotating the array, the operator can not recognize what plane is being scanned. This also may cause a long and inaccurate examination.

The above-mentioned problems may occur not only in transesophageal probes but also in puncture, endorectum, endovaginal or intraoperative probes.

SUMMARY OF THE INVENTION

Accordingly, it is an object of the present invention to provide an ultrasound diagnosis apparatus having a probe with a rotatable transducer wherein an operator can confirm an imaging angle to be examined.

It is a further object of the present invention to provide an ultrasound probe having a rotatable transducer wherein an operator can confirm an imaging angle to be examined.

It is still a further object of the present invention to provide an ultrasound diagnosis apparatus having a probe with a rotatable transducer wherein a rotation angle can be detected precisely.

It is yet further object of the present invention to provide an ultrasound probe having a rotatable transducer wherein a rotation angle can be detected precisely.

In accordance with the present invention, the foregoing objects, among others, are achieved by providing an ultrasound probe comprising a hollow housing provided at one end of the insertion portion, and a rotation portion including a transducer rotatably mounted in the housing, wherein a mark for indicating a direction of the transducer is provided on a surface of the rotation portion.

In accordance with another aspect of the present invention, the above-mentioned objects are achieved by providing an ultrasound diagnosis apparatus for obtaining ultrasound images of a patient, having a probe to be inserted into a body cavity of the patient and display means for displaying the ultrasound images, the probe comprising an insertion portion having a flexible tubular body, a hollow housing provided at one end of the insertion portion, and a rotation portion including a transducer rotatably mounted in the housing, wherein a mark for indicating a direction of the transducer is provided on a surface of the rotation portion.

In accordance with another aspect of the present invention, the above-mentioned objects are achieved by providing an ultrasound probe for insertion into a body cavity of a patient to obtain ultrasound images of the patient, comprising an insertion portion having a flexible tubular body, a hollow housing provided at one end of the insertion portion, a transducer provided in the housing, being rotatable around an axis perpendicular to a surface of the transducer, a motor for rotating of the transducer, disposed in the housing, and operation means for operating the motor, electrically connected to the motor, provided at the other end of the insertion portion.

In accordance with another aspect of the present invention, the above-stated objects are achieved by provided an ultrasound diagnosis apparatus for obtaining ultrasound images of a patient, having a probe to be inserted into a body cavity of the patient and display means for displaying the ultrasound images, the probe comprising an insertion portion having a flexible tubular body, a hollow housing provided at one end of the insertion portion, a transducer rotatably mounted in the housing, a motor for rotating of the transducer disposed in the housing, and operation means for operating the motor, electrically connected to the motor, provided at the other end of the insertion portion.

In accordance with another object of the present invention, the above-stated objects are achieved by providing an ultrasound probe for insertion into a body cavity of a patient to obtain ultrasound images of the patient, comprising an insertion portion having a flexible tubular body, a hollow housing provided at one end of the insertion portion, a transducer provided in the housing, being rotatable around an axis perpendicular to a surface of the transducer, and detection means for electrically detecting a rotation angle of the transducer, being connected to the transducer in the housing.

There has also been provided, in accordance with further object of the present invention, an ultrasound diagnosis apparatus for obtaining ultrasound images of a patient, having a probe to be inserted into a body cavity of the patient and display means for displaying the ultrasound images, the probe comprising an insertion portion having a flexible tubular body, a hollow housing provided at one end of the insertion portion, an transducer of a plurality of transducer elements, provided in the housing, being rotatable around an axis perpendicular to a surface of the transducer, and detection means for electrically detecting a rotation angle of the transducer, being connected to the transducer in the housing.

There has also been provided, in accordance with yet further object of the present invention, an ultrasound probe for insertion into a body cavity of a patient to obtain ultrasound images of the patient, comprising an insertion portion having a flexible tubular body, a hollow housing provided at one end of the insertion portion, a transducer rotatably provided in the housing, a pulley coaxially connected to the transducer, being rotatable in connection with the transducer, rotating means for rotating the pulley, having a string-like body, operating means for operating the rotating means such that the transducer is rotated in a desired direction provided at the other end of the insertion portion, and slack removing means for removing a slack of the rotating means provided in the middle of the wire means.

There has also been provided, in accordance with yet further object of the present invention, an ultrasound diagnosis apparatus for obtaining ultrasound images of a patient, having a probe to be inserted into a body cavity of the patient and display means for displaying the ultrasound images, the probe comprising an insertion portion having a flexible tubular body, a hollow housing provided at one end of the insertion portion, a transducer elements rotatably provided in the housing, a pulley coaxially connected to the transducer, being rotatable in connection with the transducer, rotating means for rotating the pulley, having a string-like body, operating means for operating the rotating means such that the transducer is rotated in a desired direction provided at the other end of the insertion portion, and slack removing means for removing a slack of the rotating means provided in the middle of the wire means.

There has also been provided, in accordance with yet further object of the present invention, an ultrasound probe for insertion into a body cavity of a patient to obtain ultrasound images of the patient, comprising an insertion portion having a flexible tubular body, a hollow housing provided at one end of the insertion portion, a transducer rotatably provided in the housing, a pulley coaxially connected to the transducer, being rotatable in connection with the transducer, rotating means for rotating the pulley, having a string-like body, operating means for operating the rotating means such that the transducer is rotated in a desired direction provided at the other end of the insertion portion, and indication means for indicating a rotation angle of the transducer.

There has also been provided, in accordance with yet further object of the present invention, an ultrasound diagnosis apparatus for obtaining ultrasound images of a patient, having a probe to be inserted into a body cavity of the patient and display means for displaying the ultrasound images, the probe comprising an insertion portion having a flexible tubular body, a hollow housing provided at one end of the insertion portion, a transducer rotatably provided in the housing, a pulley coaxially connected to the transducer, being rotatable in connection with the transducer, rotating means for rotating the pulley, having a string-like body, operating means for operating the rotating means such that the transducer is rotated in a desired direction provided at the other end of the insertion portion, and indication means for indicating a rotation angle of the transducer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

For a more complete understanding of the present invention, reference will be made to the following detailed explanations in conjunction with the accompanying drawings in which:

FIG. 9 is a schematic view of a second embodiment.

FIG. 11 is a longitudinal sectional view of a third embodiment.

FIGS. 19A and 19B show modified examples of the rotation angle indicators.

FIG. 21A is a top view of a probe including a rotation angle indicator provided not coaxially to a rotation knob and FIG. 21B is a longitudinal sectional view thereof.

DESCRIPTION OF PREFERRED EMBODIMENTS

Referring now to figures, embodiments of the present invention will be described below.

Figures 1, 2:
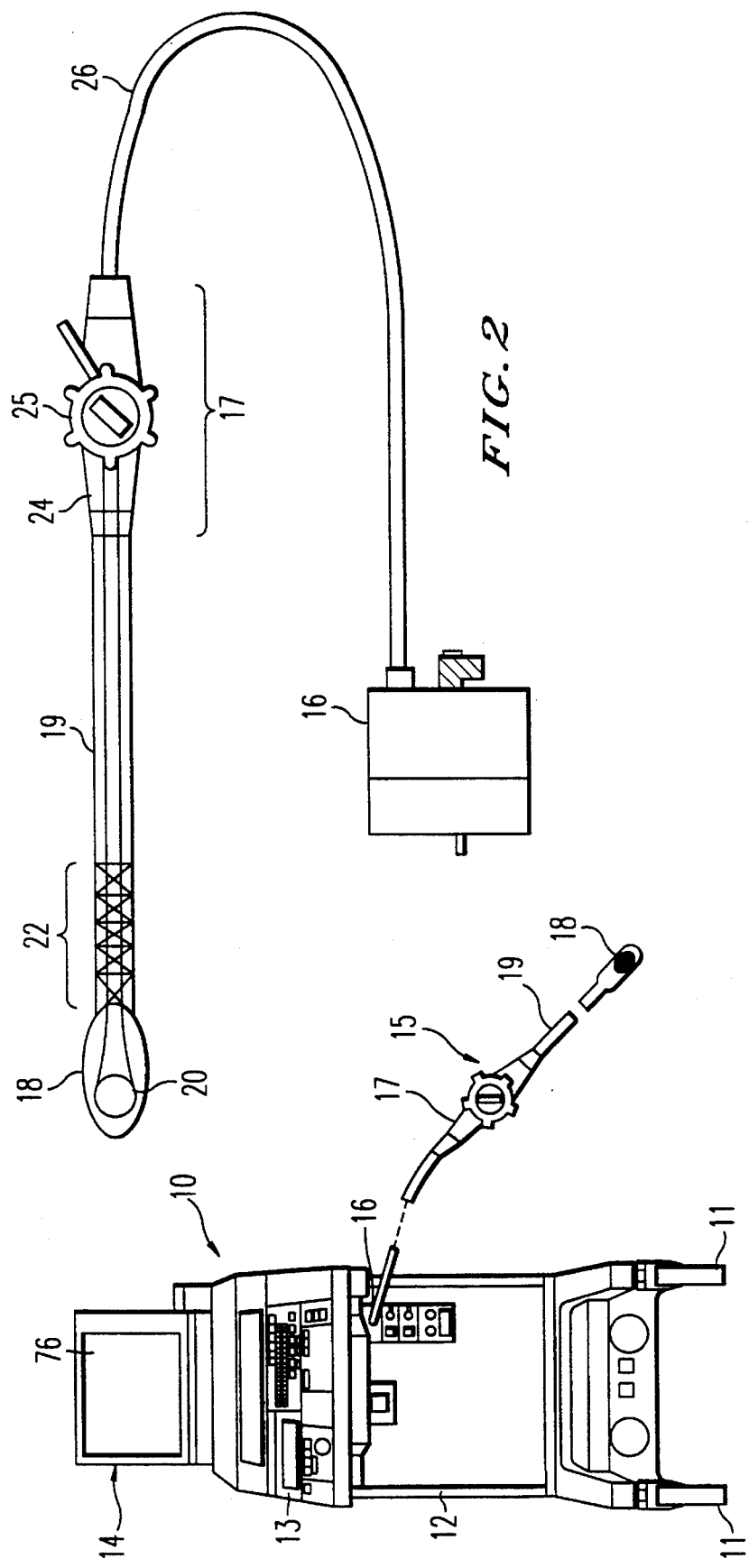
FIG. 1 shows a whole view of an ultrasound diagnosis apparatus.
FIG. 2 shows a schematic view of an ultrasound probe.

FIG. 1 shows a whole view of an ultrasound diagnosis apparatus 10. The ultrasound diagnosis apparatus 10 comprises a main unit 12 having casters 11 at the bottom thereof. On the top of the main unit 12, there provided an operation panel 13 having a keyboard and a display unit 14, such as a CRT, for displaying ultrasound images. A probe unit 15 is detachably connected to the main unit 12 through a probe connector 16. The probe unit 15 shown in FIG. 1 is a transesophageal type. Various types of probes, such as convex, sector, linear and oblique, can be connected to the main unit 12.

FIG. 2 shows a schematic view of a probe unit of a first embodiment of the present invention. The probe unit 15 is a multi-plane TEE probe to be inserted transesophageally into an upper digestive tract, such as an esophagus or stomach, for imaging of a heart, etc. The probe 15, having a shape similar to an endoscope, comprises a flexible tubular insertion part 19, made of resin, for example, to be inserted into the upper digestive tract. A probe head 18 provided at the end of the insertion part 19 comprises a transducer array 20 with a flat circular shape. The transducer array 20 is divided into a plurality of piezo-electric ceramic elements, each emitting ultrasound waves in a plane perpendicular to the surface of the array 20 to perform sector scanning electronically. Each element may have an elongated rectangular shape provided such that the longer sides are adjacent to one another. By rotating the transducer array 20, a scanning plane of the ultrasound wave rotates to obtain cross-sectional images along various angles without changing the direction of the probe head 18. This is advantageous in medical use, especially imaging cross-sectional images along the transverse or longitudinal axes of a heart.

The insertion part 19 comprises an angle portion 22 to be bent up and down or left and right, which is connected to the probe head 18 for varying the direction thereof and for stick to the inner wall of a body cavity. The angle portion 22 is bent by pulling one of two pairs of wires disposed inside the insertion part 19.

At the end of the insertion part 19 opposite to the probe head 18, an operational part 17 is connected not to be inserted into the body cavity but to be operated by an operator, such as a doctor. The operational part 17 comprises a rotation knob 24 for rotating the transducer 20. Two flexion knobs 25 for bending the angle portion 22 up-and-down and left-and-right may be provided coaxially to the rotation knob 24. Preferably, these three knobs may different diameters and different heights. The operational part 17 is connected to the main unit 12 through a cable part 26 and the connector 16.

Figure 3A:
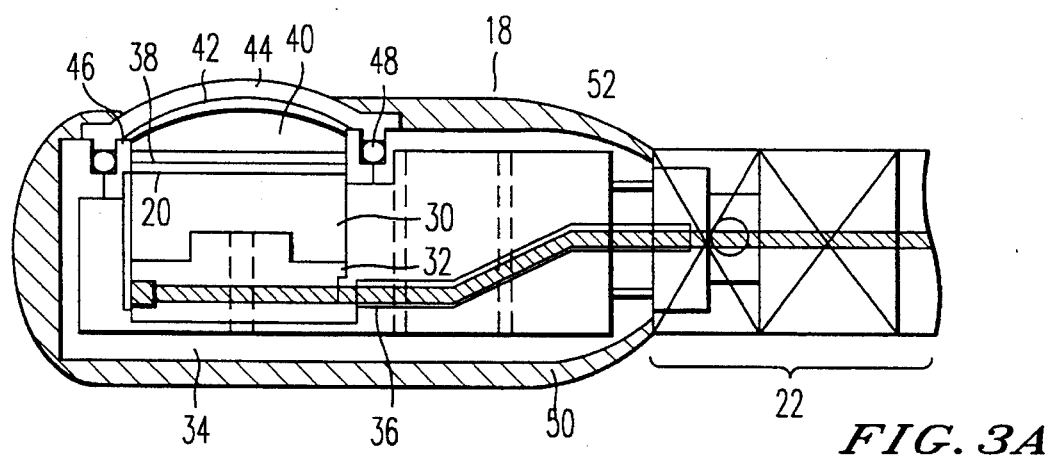
FIG. 3A shows a longitudinal sectional view of a probe head of the ultrasound probe of a first embodiment and FIG. 3B shows a cross-sectional view thereof.
Figure 3B:
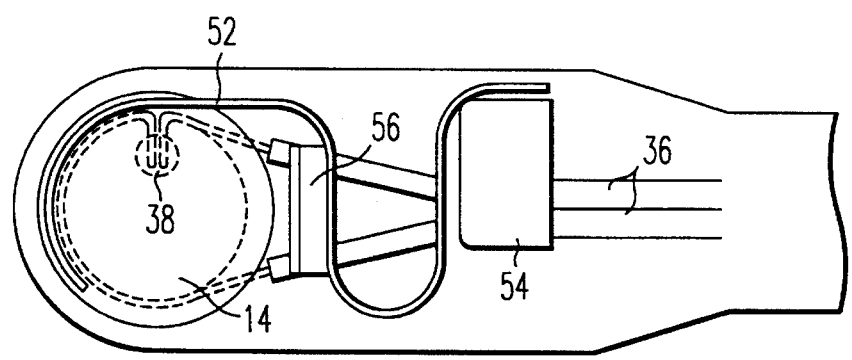

FIG. 3A shows a longitudinal sectional view of the probe head 18 and FIG. 3B shows a cross-sectional view thereof. The circular transducer 20 is mounted on a cylindrical backing portion 30 which is fixed on a driven pulley 32. The driven pulley 32 is rotatably mounted in a housing 34 which contains elements for the probe head 18. A pair of wires 36 for rotating the transducer 20 are wound around the driven pulley 32. Each of end portions of the wires 36 is fixed to the driven pulley 32 at a fixing point 38. By pulling one of the wires 36 toward the operational part 17, the other wire is wound around the driven pulley 32 and the transducer 20 is rotated. Instead of the wires 36, a belt may be used.

Outputs of the piezo-electric elements of the transducer 20 are electrically connected to the main unit 12 through conductors printed on a flexible printed circuit board 52 and conductor cables disposed through the insertion part 19. Through these conductors and the cables, high voltage pulses for driving the transducer 20 are supplied from the main unit 12 and ultrasound signals received by the transducer 20 is transmitted to the main unit 12. Each of the drive pulses supplied with a predetermined delay time to form a sector ultrasound beam. The flexible printed circuit board 52 is also connected to the ground. The flexible board 52 is wound around the backing portion 30 and the driven pulley 32. The end of the flexible board 52 is fixed to the backing portion 30 and the other end is fixed to a guide 54. Another guide 56 is provided between the guide 54 and the transducer 20, and the flexible board 52 can be slackened between the guides 54, 56.

An acoustic lens 40, with a spherical or cylindrical shape, is mounted on the transducer 20 with an acoustic matching layer 38 therebetween, which matches acoustic impedance. Preferably, the lens 40 is made of silicon. On the acoustic lens 40, an acoustic window 44 is mounted to the housing 34 with an O-ring 48 and a sealing 46 therebetween. The space between the lens 40 and the window 44 is filled with acoustic liquid 42, such as castor oil. The window 44 is made of transparent material, such as plastics. The outer surface of the housing 34 except for the window 44 is molded by epoxy resin, for example, to form a waterproof mold case 50.

Figure 4:
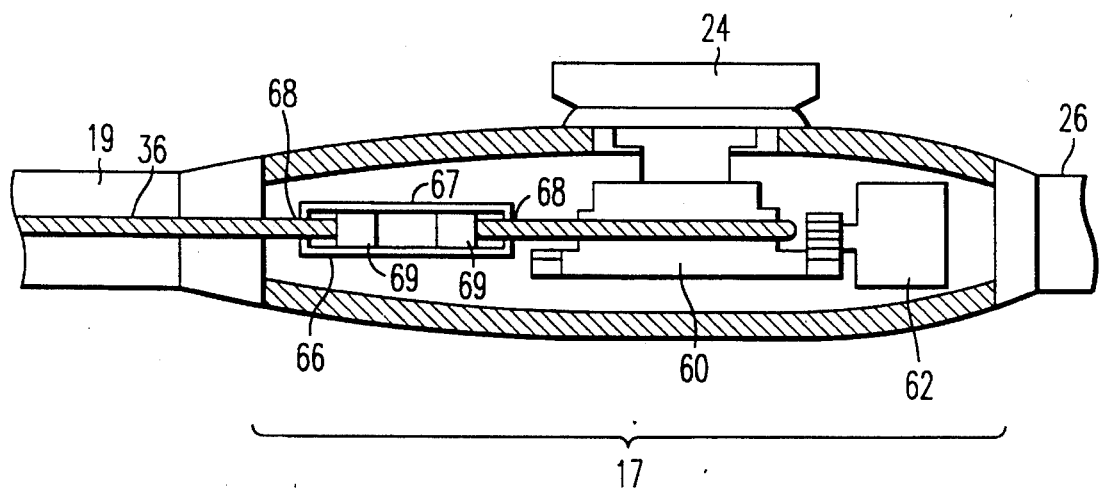
FIG. 4 shows a longitudinal sectional view of an operation part of the probe.

FIG. 4 shows a longitudinal section of the operational part 17. End portions of the rotation wires 36 are elongated to the operational part 17 and wound around a drive pulley 60 which is connected to the rotation knob 24. By rotating the rotation knob 24, one of the wires 36 is wound up and tensed to rotate the driven pulley 32 and the transducer 20.

Figure 5:
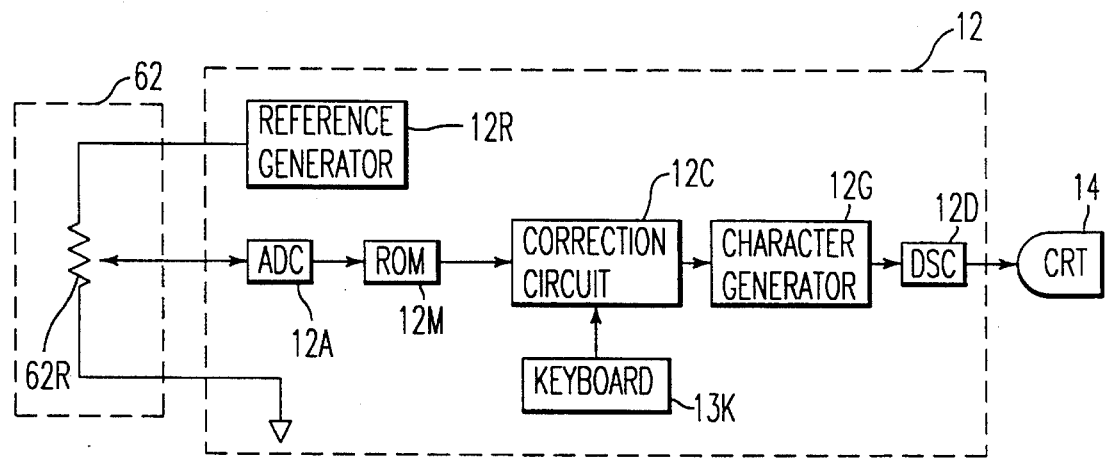
FIG. 5 is a block diagram for electrically detecting and displaying a rotation angle.
Figure 6:
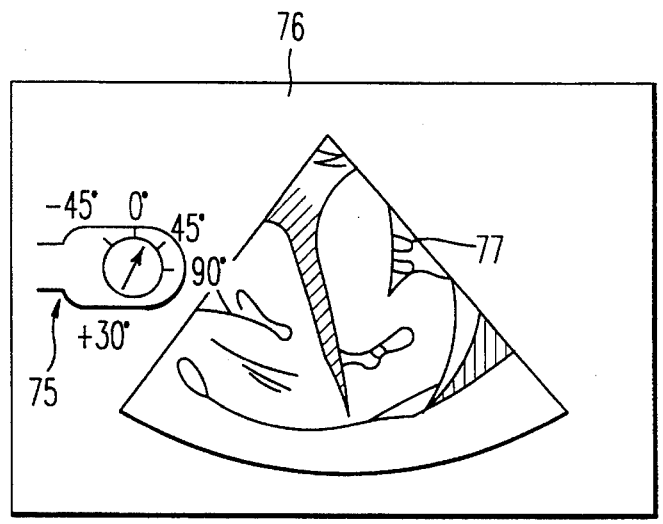
FIG. 6 is a display example of a graphical indicator of the rotation angle.

To detect a rotation angle of the transducer 20, a rotary encoder 62 is provided to the driven pulley 60 with a gear therebetween. The rotary encoder 62 can be a conventional potentiometer which outputs a variable voltage representing the rotation angle. FIG. 5 shows an example of a block diagram for detecting and displaying the rotation angle. A reference voltage generator 12R in the main unit 12 generates a constant reference voltage, for example, 10 V. The encoder 62 comprises a variable resistor 62R which resistance value varies as the rotation knob 24 rotates to output a variable voltage to the main unit 12. The output from the encoder 62 is converted to a digital signal by an analog-to-digital converter 12A in the main unit 12. The converted digital signal is inputted into a ROM 12M having a look-up table, which stores various angle values addressed by various voltage values to be converted to an angle value. The angle value is inputted into a graphical character generator 12G through a correction circuit 12C. The graphical character generator 12G generates a graphical character signal according to the inputted angle value. The graphical character is inputted into the CRT 14 through a digital scan converter 12D and displayed on the CRT 14 as a graphical indicator 75. An example of the graphical indicator 75, displayed on the same screen 76 as an ultrasound cross-sectional image 77, is shown in FIG. 6. In this embodiment the graphical indicator 75 includes an arrow pointing the detected angle in a scale imitating the shape of the probe head and a numeral thereunder.

In the intermediate of each wire 36, a slack remover 66 is provided. The slack remover 66 comprises a cylindrical body 67 with closed ends, each of which has a hole 68 for the wire 36 to penetrate therethrough. Inside the cylindrical body 67, the wire 36 is divided and each ends thereof has a stopper 69 with a diameter larger than the hole 68. The distance between the stoppers 69 in one of the slack removers 66 is shortened when the drive pulley 60 is being rotated. This distance change between the stoppers 69 prevents the wires 36 to be slackened. Since no slack occurs, the wires 36 between the driven pulley 32 and the slack removers 66 are always tensed during the drive pulley 66 is being rotated. This can prevent errors in detecting a rotation angle even if the wires 66 is undesirably extended after a long use.

Figure 7A:
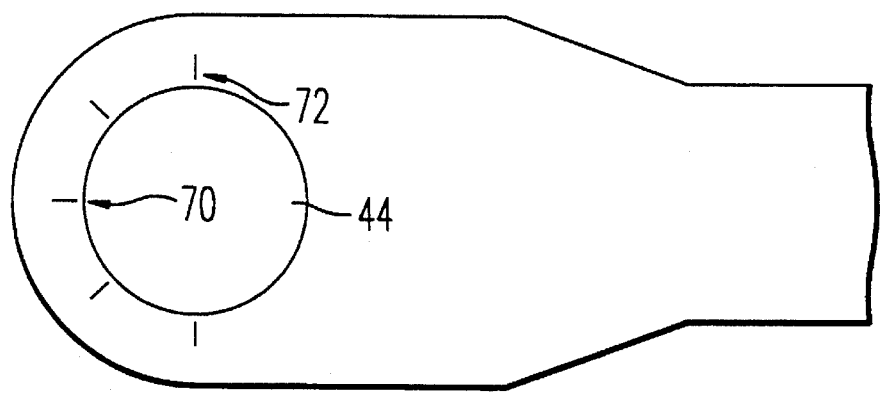
FIGS. 7A and 7B show examples of marks each provided on the transducer.
Figure 7B:
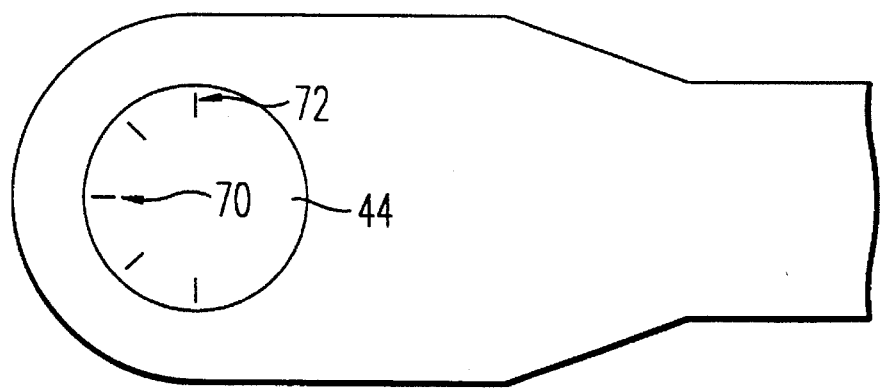

In this embodiment, as shown in FIG. 7A, a mark 70 for indicating a direction of the transducer 20 is formed on the surface of the transducer 20. The mark 70 can be viewed through the transparent window 44. A scale 72 for indicating the rotation angle in connection with the mark 70 is provided on the surface of the mold case 50 around the window 44. The scale 70 may be formed on the surface of the window 44 as shown in FIG. 7B. The mark 70 is formed by printing and the scale is formed by stamping.

The mark 70 can be formed on any structure which rotates with the transducer 20 and can be viewed through the window 44, such as a frame structure provided around the transducer 20. For example, a small notch as the mark 70 may be formed on the surface of the sealing 46.

The operator can confirm whether the transducer 20 rotates at a desired angle by viewing the mark 70 and the scale 72 when operating the rotation knob 24. The operator can also confirm whether displayed angle detected by the rotary encoder 62 is identical to the angle indicated by the mark 70 and the scale 72. If the displayed angle is not identical, it can be corrected by inputting the correct angle, which is indicated by the mark 70 and the scale 72, into the correction circuit 12C from a keyboard 13K, for example, of the operation panel 13. In the correction circuit, the difference value between the inputted angle and the output value from the ROM 12M is calculated and stored therein. Then the difference value is added to the output from the ROM 12M. Thus, the correct angle can be displayed even if the wire 36 is undesirably extended.

On the contrary to the above, the mark 70 may be formed on the window 44 or mold case 50 and the scale 72 may be formed on the transducer 20.

Figure 8:
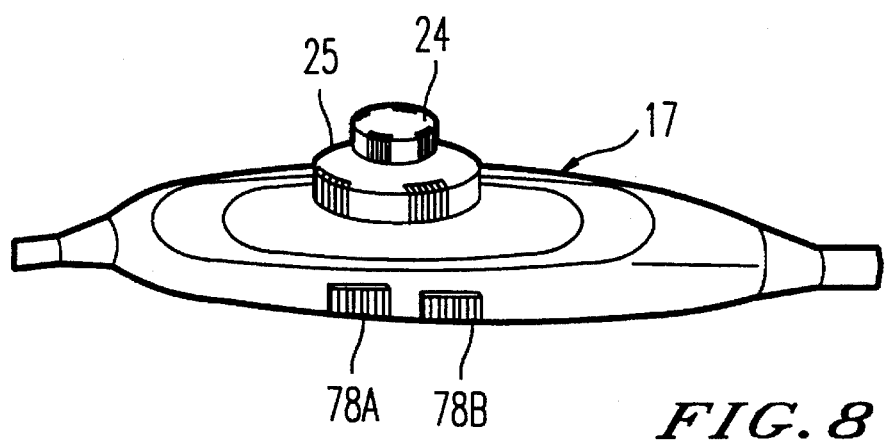
FIG. 8 is a perspective view of an operation portion having switches of a motor.

Instead of or in addition to the rotation knob 24, a motor may be disposed in the operational part 17 for rotating the drive pulley 60. As shown in FIG. 8, switches 78A and 78B are provided on the operational part 17. The transducer 20 turns to the right during the switch 78A is on and it stops when the switch 78A is released. The transducer 20 turns to the left during the switch 78B is on. The operator can confirming the rotation angle displayed on the screen 76, pushing the switches 78A or 78B. In this modified embodiment, a rotation knob is not necessary. In addition, operation of the angle portion may also be driven by another motor.

In the first embodiment as described above, the actual rotation angle corresponding to the rotation of the rotation knob can be confirmed with the mark and the scale, which enables an accurate setting of the scanning plane to be examined. Therefore, diagnosis can be more accurate and the apparatus can be easily inspected. In this embodiment, the scale on the window or the mold case is not essential for the scope of the invention and can be omitted.

A second embodiment of the present invention will be described below. Parts substantially same as the previous embodiment have the same numerals and will not be described in detail.

Figure 10:
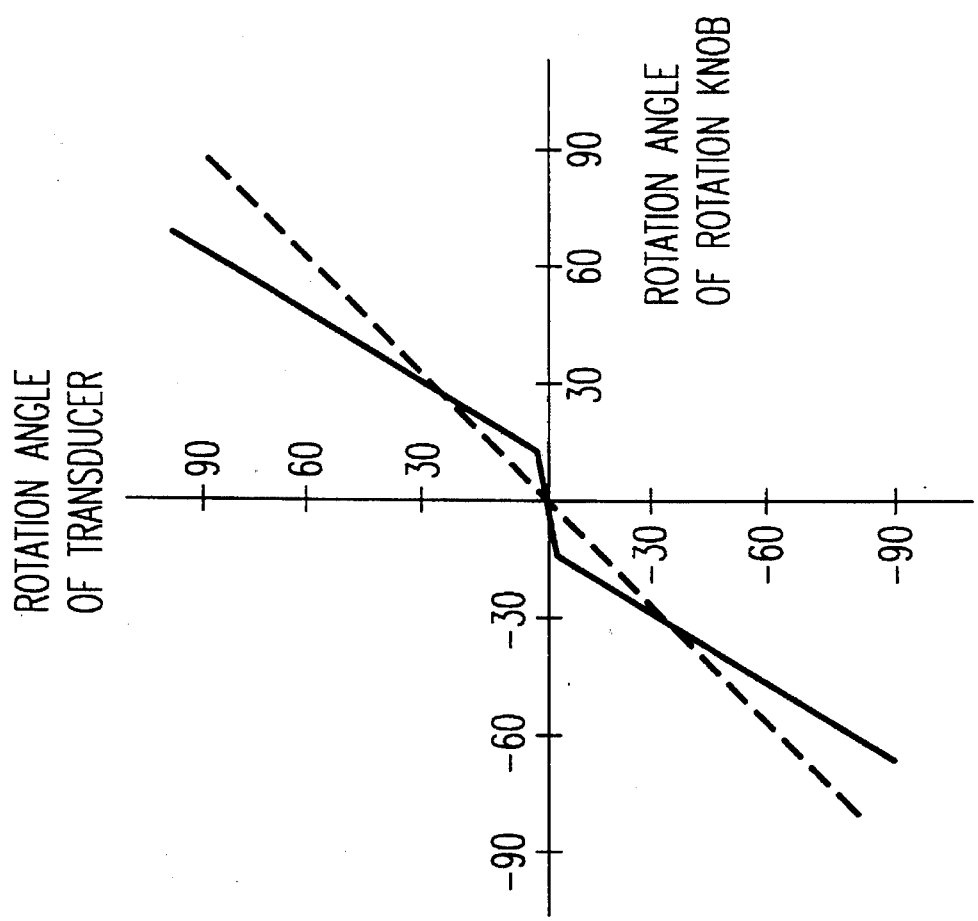
FIG. 10 is a graph showing a characteristic of rotation of a rotation knob.

As shown in FIG. 9, the ultrasound probe 15 as described in the first embodiment comprises the slack removers 66 in the intermediate of the wires 36 between the driven pulley 32 and the drive pulley 60, which causes delayed response to the rotation of the rotation knob 24. There is a non-response period in the rotation characteristic representing the relationship between the rotations of the transducer 20 and the rotation knob 24 as shown in FIG. 10 as a continuous line. Characteristic of this non-responsive period depends on the extent of the extension of the wire 36 and it is difficult to detect precisely. Therefore, an error in the displayed angle may occur since the look-up table in the ROM 12M has a linear, theoretical characteristic.

In the second embodiment, as shown in FIG. 9, linear encoders 79 for detecting the movements of the wires 36 are provided between the transducer 20 and the slack removers 66. Each of the linear encoders 79 comprises a potentiometer outputting a variable voltage according to the movement of the wire 36. Since the wires 36 between the transducer 20 and the slack removers 66 are always tensed during the rotation of the transducer 20 and there is no non-response period, the actual rotation angle of the transducer 20 and the displayed angle detected by the linear encoder 79 can be identical.

For rotating the driven pulley 32 connected to the transducer 20 at 90 degrees, the movement length of the wire 36 is shown as:

$$2\pi r_r \times (\pm 90)/360 = \pm(\frac{1}{2})\pi r_r,$$

where the diameter of the driven pulley 32 is $r_r$. When $r_r=4$ mm, the movement length of the wire 36 is approximately 6.28 mm. For this rotation of the transducer 20, the rotation knob 24 is required to rotate at the angle $\pm 90° \times (r_r/r_n) \pm \alpha$, where $r_n$ is the diameter of the drive pulley and $\alpha$ is a non-response angle caused by the slack remover 66. For example, when $r_n=8$ mm, the required rotation angle of the rotation knob 24 is $\pm 45° \pm \alpha$. A linear encoder with a 13 mm stroke can detect this angle.

According to the second embodiment as described above, an accurate rotation angle of the transducer can be detected, not interfered by the non-response angle caused by the slack removers. The operator can set an imaging angle to a desired angle for obtaining a cross-sectional image of a heart correctly along the transverse or longitudinal axis, for example.

In addition to the above, for preventing detection errors, an error preventing circuit may be provided, which determines that an error occurs when only one of the linear encoders 79 outputs a signal and prevents to display the angle. If two encoders 79 output different values, an average value thereof may be displayed.

A third embodiment for a more precise detection will be described below referring to FIG. 11. A rotary encoder 80 for detecting the rotation angle of the transducer 20 is mounted coaxially to the driven pulley 32 in the probe head 18. According to the third embodiment, the rotation angle of the transducer 20 can be detected directly to set the imaging plane in a desired angle correctly.

Figure 12:
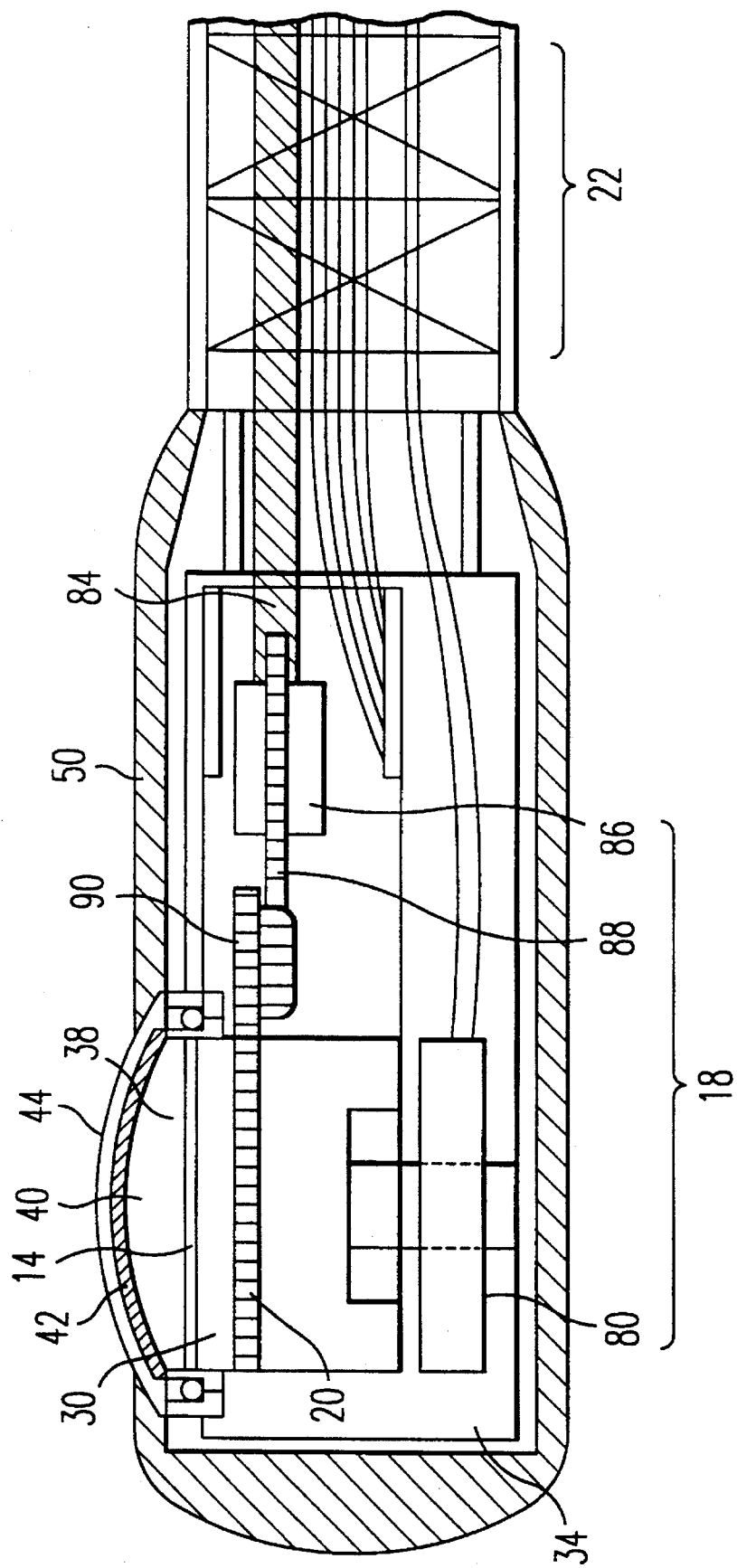
FIG. 12 is a longitudinal sectional view of a fourth embodiment.

A fourth embodiment, employing a shaft-drive system, is shown in FIG. 12. Similar to the third embodiment, a rotary encoder 80 is mounted coaxially to the driven pulley 32 for directly detecting the rotation angle of the transducer 20. A shaft 84 is provided through the insertion part 19 instead of the wire 36. The rotation power of the rotation knob 24 is transmitted through the shaft 84 and the rotation of the shaft 84 is transmitted to the driven pulley 32 through a worm gear 86, a worm wheel 88 and a gear 90. The shaft 84 may be rotated by a motor mounted in the operational part 17.

As described in the third and fourth embodiments, by directly detecting the rotation angle of the transducer 20 by the rotary encoder 80, the rotation angle can be correctly detected not being interfered by undesired extension of the wires 36 or a backlash of the rotation knob to set an imaging angle quickly and to achieve a better throughput.

Embodiments employing a source of a rotation power, e.g., a motor, in the probe head 18 will be described.

Figure 13:
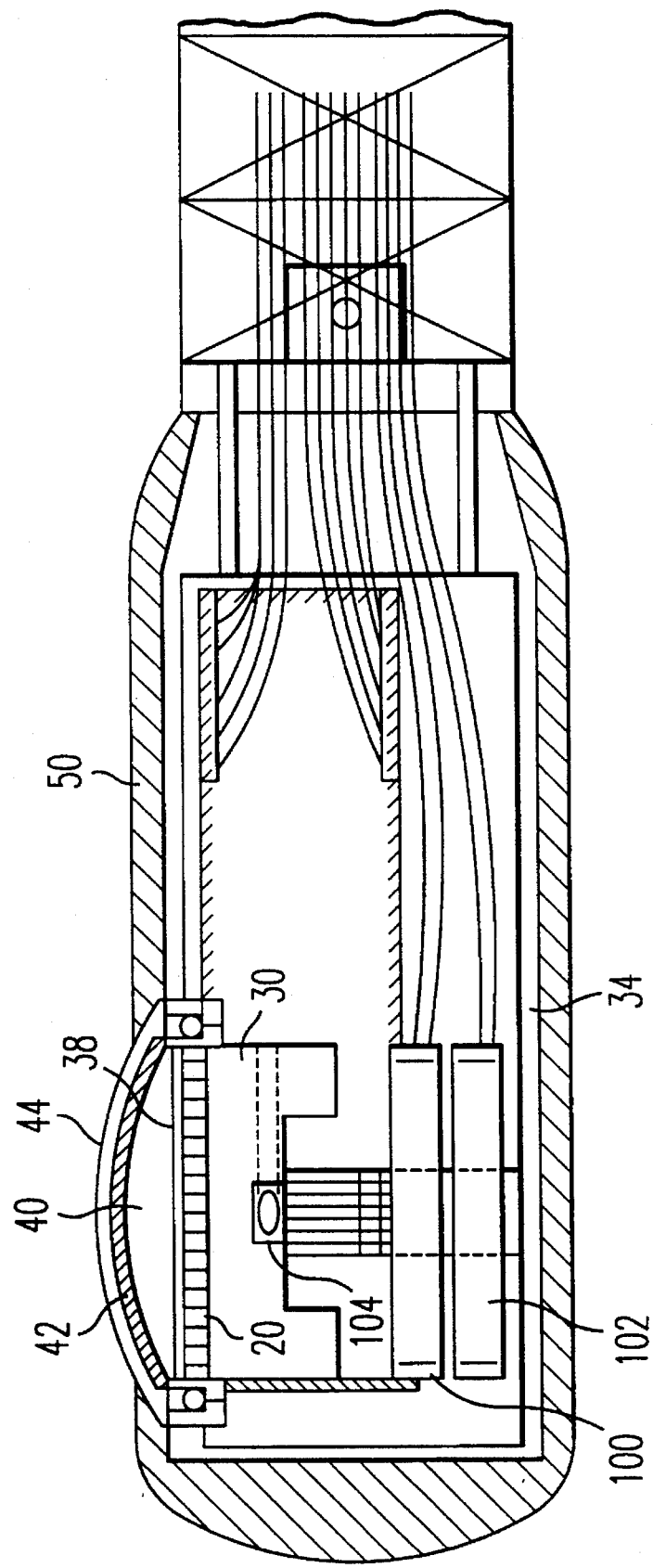
FIG. 13 is a longitudinal sectional view of a fifth embodiment.

FIG. 13 shows a fifth embodiment comprising a motor 100 mounted coaxially to the transducer 20. In this embodiment, a rotary encoder 102 is also mounted coaxially to the transducer 20.

A thermistor 104 is mounted on the backing portion 30. The thermistor may be a conventional thermal sensor for sensing temperature of the transducer to overheat which may cause a pain or scald in a body cavity of the patient. When the thermistor 104 detects that the temperature is over a predetermined value, the transducer 20 is turned off and a warning message is displayed on the display unit 14.

According to the fifth embodiment, since the motor mounted in the probe head directly rotates the transducer, the transducer can always be rotated rapidly and the imaging angle can be set precisely, not interfered by the angle operation. Further, the probe has higher durability than that with a wire or shaft drive system. Furthermore, since wires or a shaft for rotating the transducer is not necessary and only wires for the angle portion and signal cables is provided inside the insertion portion, the insertion portion can be of simple structured and small sized. Moreover, since the transducer, the motor and the rotary encoder are provided coaxially, the rotation angle can be detected precisely not interfered by extension of the wires or backlash of the gears.

Figure 14:
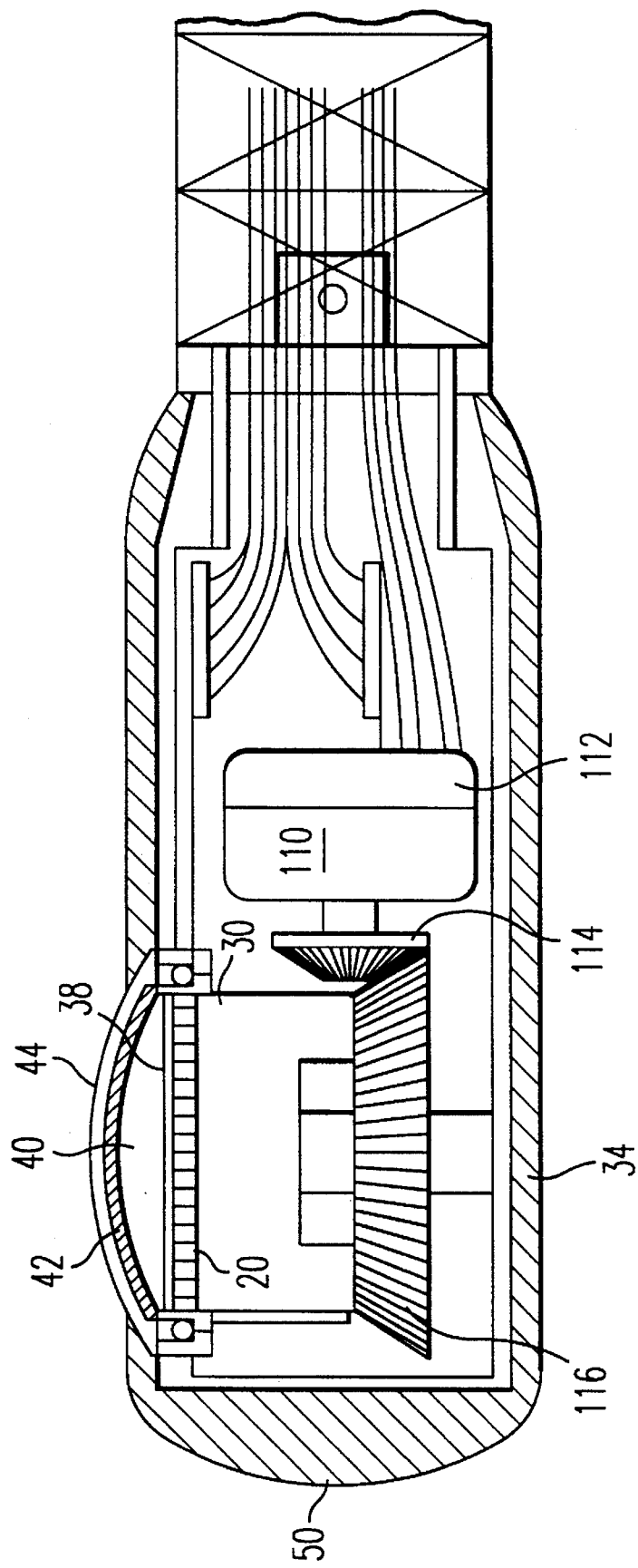
FIG. 14 is a longitudinal sectional view of a sixth embodiment.

FIG. 14 shows a sixth embodiment of the present invention. In the sixth embodiment, the locations of a motor and a rotary encoder are different from the fifth embodiment. Rotation axes of a motor 110 and a rotary encoder 112 are provided to be perpendicular to the axis of the transducer 20. The rotation power is transmitted through bevel gears 114, 116 to the transducer 20. The motor 110 and the rotary encoder 112 may be mounted in parallel with gears for connecting the rotation axes.

Figure 15:
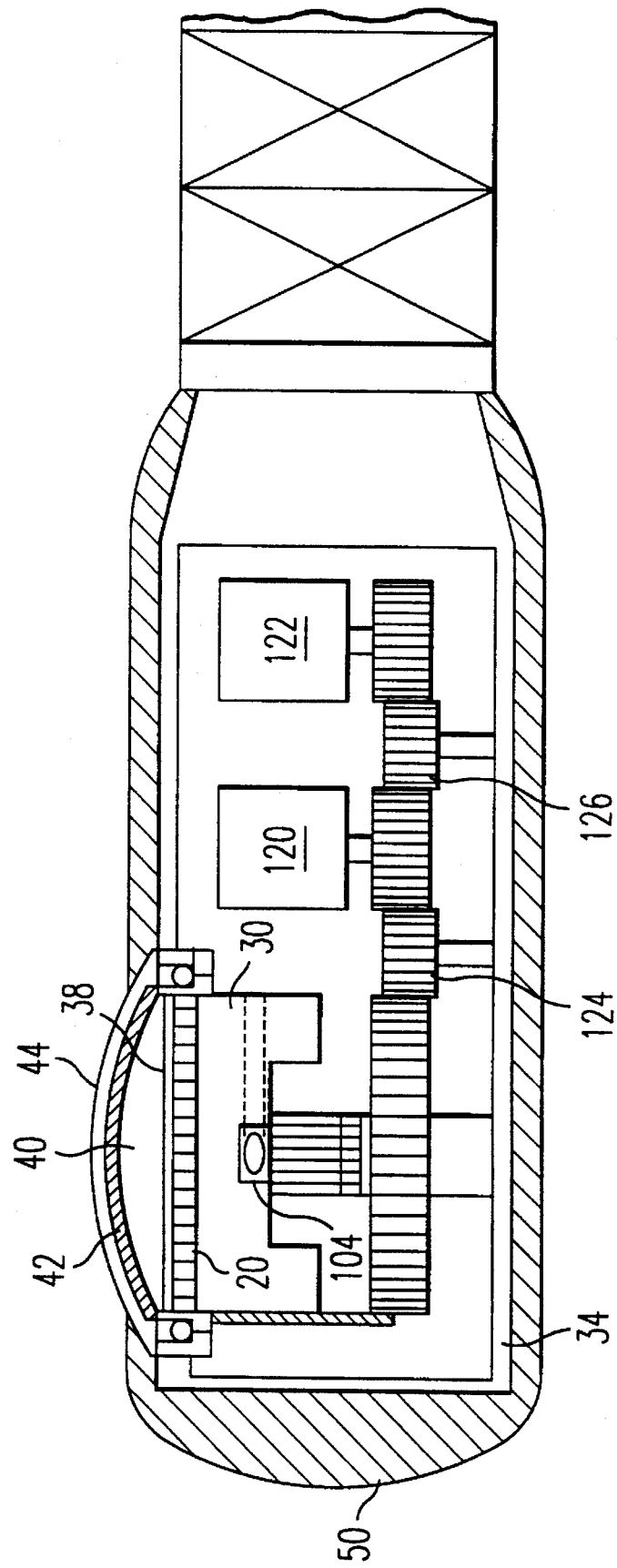
FIG. 15 is a longitudinal sectional view of a seventh embodiment.

FIG. 15 shows a seventh embodiment of the present invention. Also in the seventh embodiment, the locations of a motor and a rotary encoder are different from the fifth embodiment. Rotation axes of a motor 120 and a rotary encoder 122 are provided in parallel, not coaxially to the axis of the transducer 20. The rotation power of the motor 120 is transmitted through gears 124, 126 to the transducer 20 and the rotary encoder 122.

According to the sixth and seventh embodiments, similar to the fifth embodiment, the transducer can be rotated rapidly and precisely, and the probe has high durability and is of simple structured. Further, since the motor and the rotary encoder are not provided coaxially to the transducer, the diameter of the probe head can be small.

Figure 16:
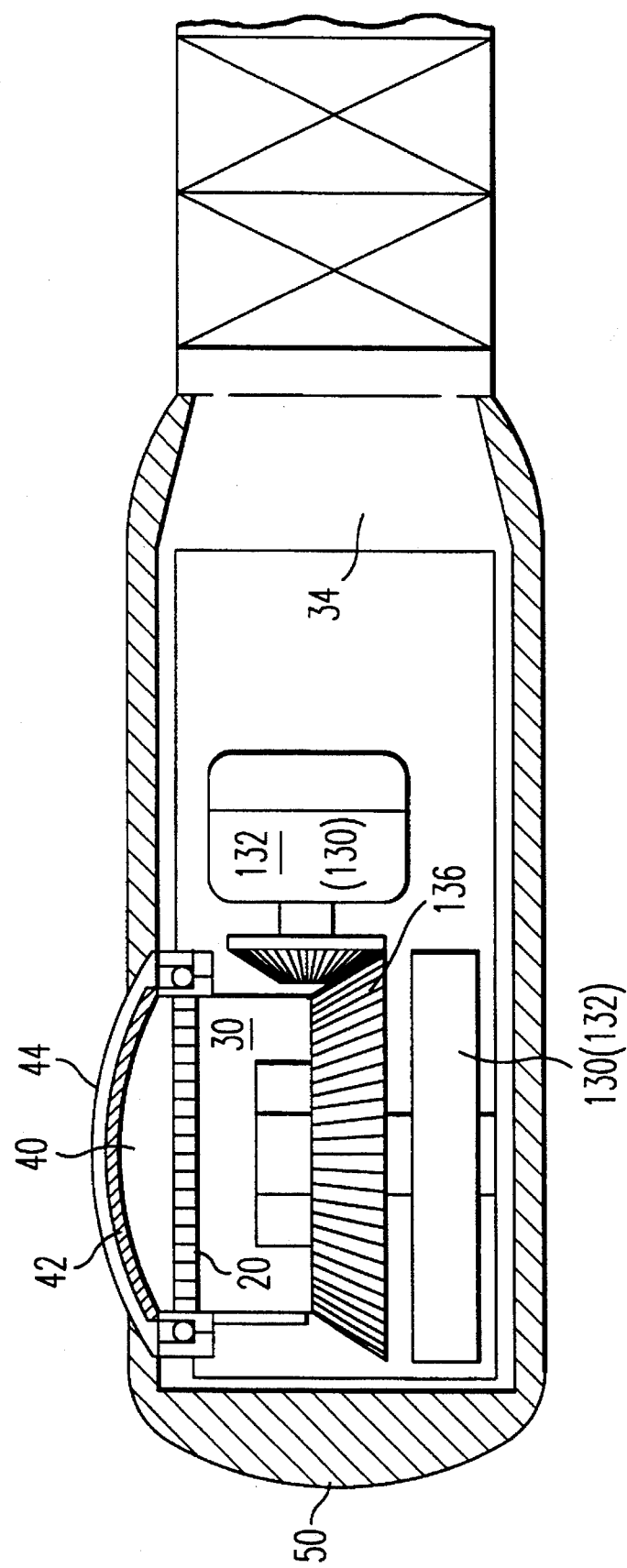
FIG. 16 is a longitudinal sectional view of an eighth embodiment.

In a sixth embodiment shown in FIG. 16, only one of a motor 130 and a rotary encoder 132 may be mounted coaxially to the transducer 20. The other element is connected to the transducer 20 through bevel gears 134, 136.

Figure 17A:
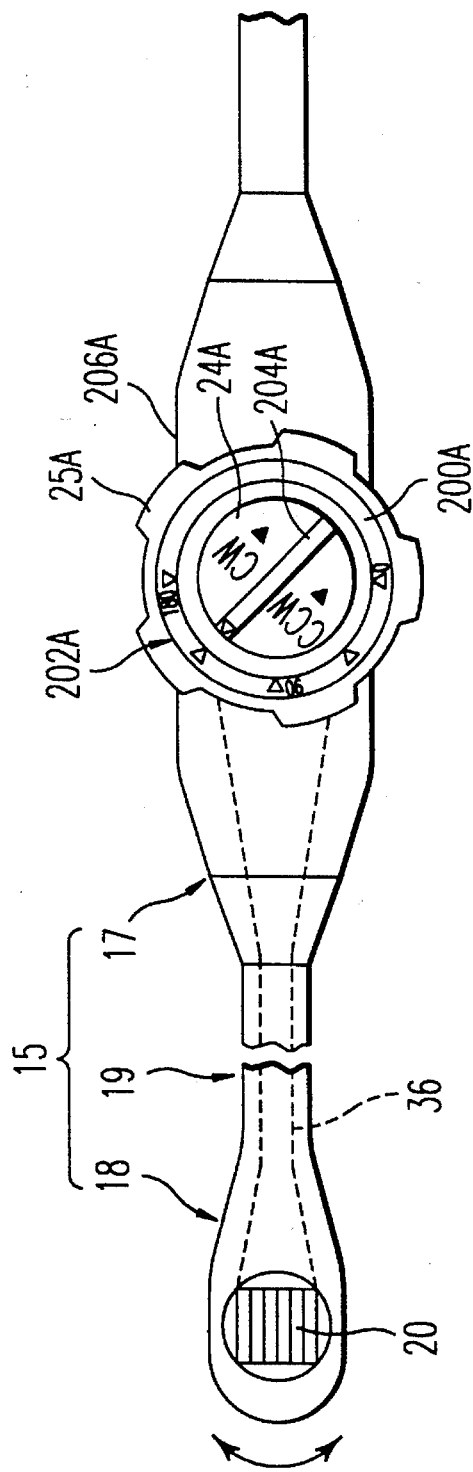
FIG. 17A is a top view of a probe including a rotation angle indicator and FIG. 17B is a side view thereof.
Figure 17B:
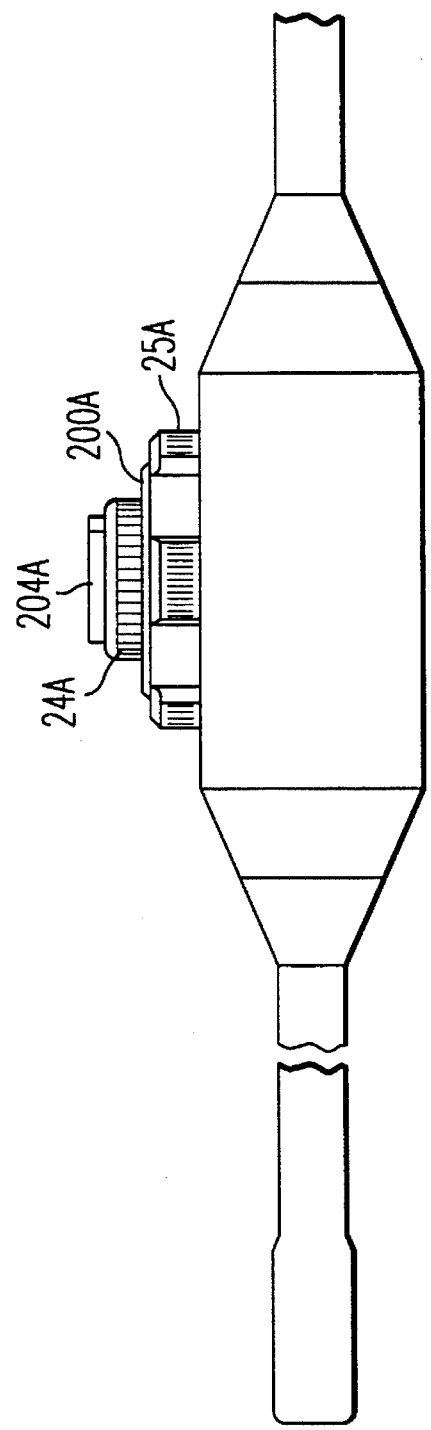

FIGS. 17A and 17B show a rotation angle indicator provided on the operation portion 17. A rotation knob 24A for rotating the transducer 20 and a flexion knob 25A for bending the angle portion 22 are mounted coaxially and these knobs are rotatable independently. The flexion knob 25A has a larger diameter and a smaller height. A stationary part 200A, on which a scale 202A is provided, is provided between the knobs 24A and 25A. The scale 202A has numerals −90°, 0° and +90°. A mark 204A and rotation directions CW, CCW are provided on the surface of the rotation knob 24A. The mark 204A may be projected from the top of the rotation knob 24A to be pinched by the operator as shown in FIG. 17B. The mark 204A and the scale 202A constitute a rotation angle indicator 206 for indicating the rotation angle of the transducer 20.

According to the rotation angle indicator on the operation portion, the operator can confirm the rotation angle of the transducer by viewing the operational portion.

Figure 18A:
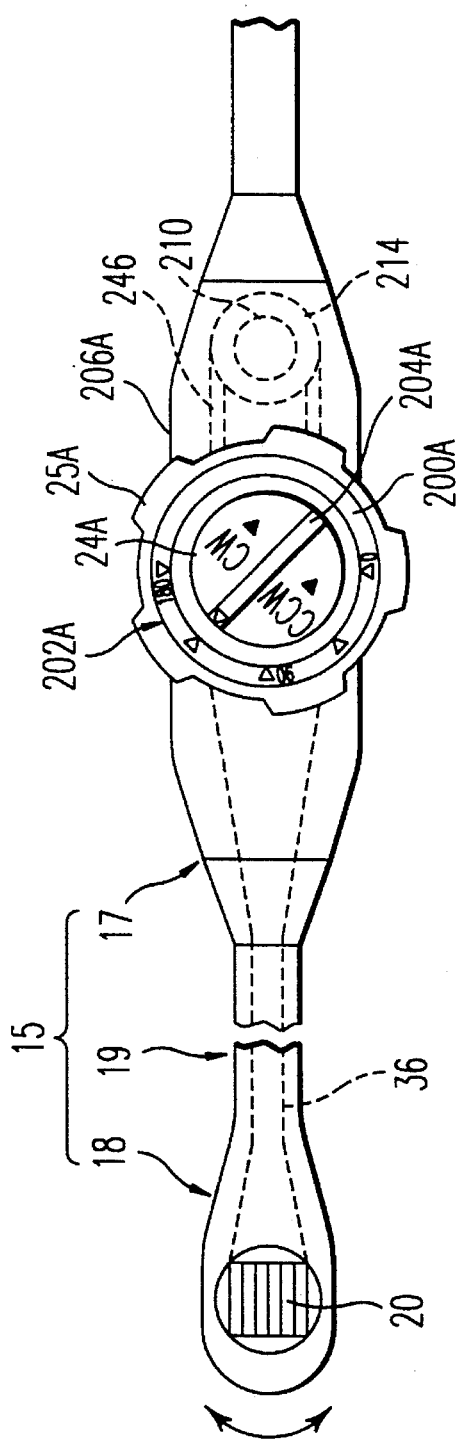
FIG. 18A is a top view of a probe including a motor in an operation portion and FIG. 18B is a longitudinal sectional view thereof.
Figure 18B:
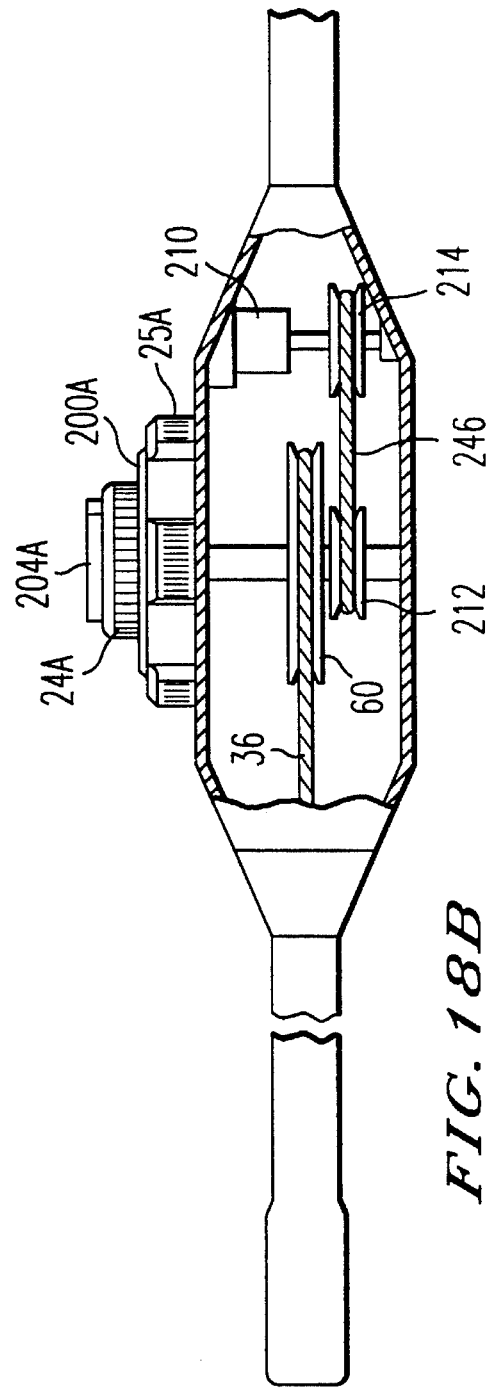

In FIGS. 18A and 18B, a reversible motor 210 is mounted in the operation portion 17. Rotation power of the motor 210 is transmitted from a pulley 214 coaxially connected to the motor 210 to another pulley 212 coaxially connected to the rotation knob 24A through a wire 216 and is also transmitted to the transducer 20 through the wire 36 from the drive pulley 60 coaxial to the pulley 212. The motor 210 drives during a switch 218 is on. The switch 218 has a similar structure to that in FIG. 8. When the motor 210 is on, the rotation knob 24A is rotated with the mark 204A which indicates the rotation angle in connection with the stationary scale 202A. The rotation may be performed manually by rotating the rotation knob 24A for finer setting.

FIGS. 19A and 19B show other examples of the rotation angle indicators 206B. In FIG. 19A, a stationary part 200B of the indicator 206B has a scale 202B with numerals 0°, 90° and 180°. In FIG. 19B, a rotation knob 24C with a scale 202C of the indicator 206C is provided around a stationary part 200C with a mark 204C.

Figure 20:
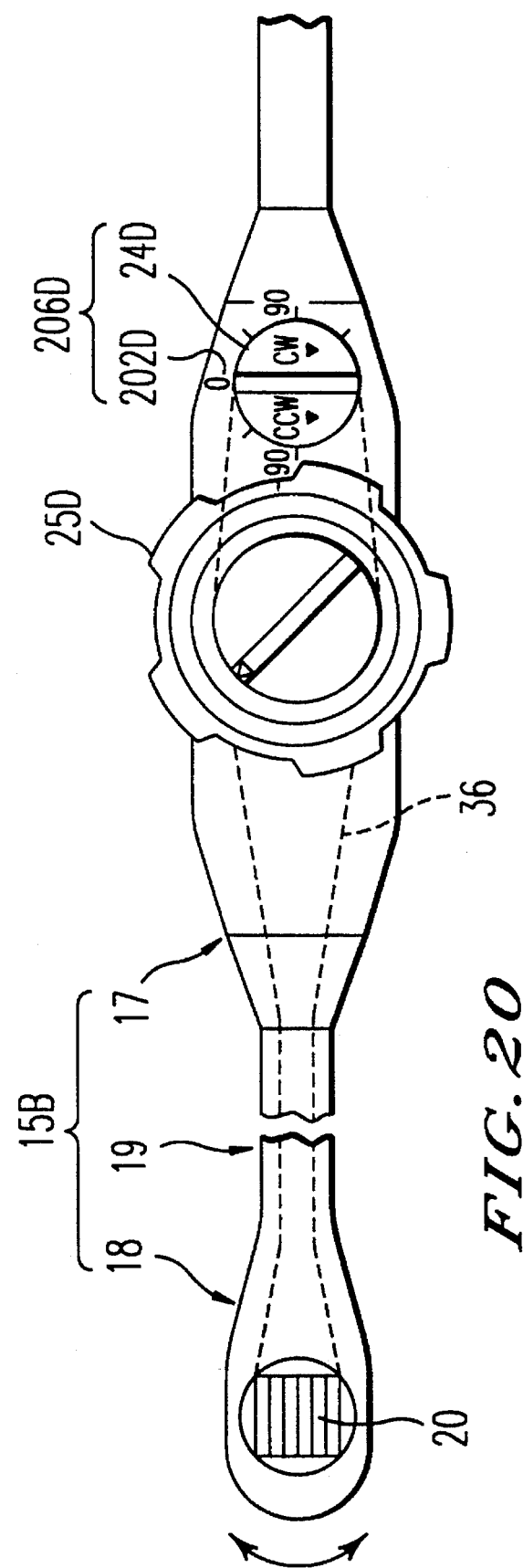
FIG. 20 is a top view of a probe including a rotation knob provided not coaxially to a flexion knob.

The rotation knob 24 may be provided not coaxially to the flexion knob 25 as shown in FIG. 20. Rotation of the rotation knob 24D is transmitted from a drive pulley 60D provided coaxially to the rotation knob 24D to the driven pulley 34 through the wire 36. A scale 202D is provided around the rotation knob 24D on the surface of the operation portion 17.

The rotation angle indicator 206E may be provided on the operation portion 17 not coaxially to the rotation knob 24 as shown in FIGS. 21A and 21B. Rotation of the rotation knob 24E is transmitted from a pulley 220E coaxial to the rotation knob 24E to another pulley 222E to rotate a rotation part 224E of the rotation angle indicator 206E.

Although the present invention has been described with reference to preferred embodiments, numerous modifications and rearrangements can be made, and still come within the scope of the invention.

Figure 22:
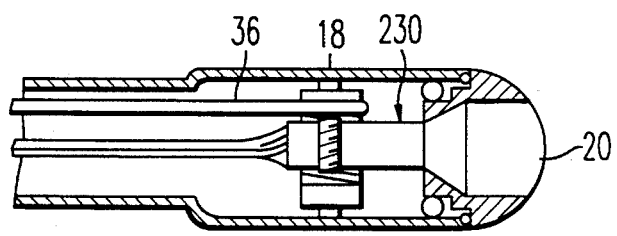
FIG. 22 shows a modified embodiment of a probe head with a transducer provided on the top thereof.

For example, a CCD for detecting an optical image may be provided in the probe head. Further, a system for rotating the transducer is not limited to the above embodiments. Instead of the pair of wires for rotating in two directions, a wire for rotating in one direction and a spring for rotating the other direction may be employed. A rotation angle detector other than a linear or rotary encoder may be employed. Further, the present invention can be employed to probes for body cavities other than TEE probes. Furthermore, the type of the transducer is not limited to phased array or sector type. Moreover, the transducer may be mounted on the top of the probe head as shown in FIG. 22. Rotation power is transmitted to the transducer 20 through a worm gear system 230 in the probe head 18.

What is claimed is:

1. An ultrasound probe for insertion into a body cavity of a patient to obtain ultrasound images of the patient, comprising:

an insertion portion having a flexible tubular body;

a hollow housing provided at one end of the insertion portion;

a transducer mounted in said housing, said transducer having a flat surface and being rotatable about an axis perpendicular to said flat surface; and a mark visible from the exterior of the housing for indicating a direction of the transducer provided on a surface of the rotation portion.

2. The ultrasound probe according to claim 1, the mark being provided on the surface of the transducer.

3. The ultrasound probe according to claim 2, the mark being printed on the surface of the transducer.

4. The ultrasound probe according to claim 1, the housing further comprising a window being transparent such that the surface of the transducer can be viewed therethrough.

5. The ultrasound probe according to claim 4, the window having a scale.

6. The ultrasound probe according to claim 1, a part of the housing which surrounds the transducer having a scale.

7. The ultrasound probe according to claim 1, further comprising a frame provided around the transducer, wherein the mark is provided on a surface of the frame.

8. The ultrasound probe of claim 1, further comprising:

a motor disposed in the housing for rotating the transducer; and operation means for operating the motor, electrically connected to the motor and provided at the other end of the insertion portion.

9. The ultrasound probe according to claim 8, the motor being connected to the transducer coaxially.

10. The ultrasound probe according to claim 8, the motor disposed parallel to the rotation axis of the transducer, being connected to the transducer with a gear therebetween.

11. The ultrasound probe according to claim 8, the operation means having a switch for electrically switching the motor.

12. The ultrasound probe according to claim 11, wherein the motor is activated during the switch is being on.

13. The ultrasound probe according to claim 11, wherein the motor rotates a predetermined angle when the switch is on.

14. The ultrasound probe according to claim 8, further comprising detection means for electrically detecting a rotation angle of the transducer, being connected to the transducer.

15. An ultrasound diagnosis apparatus for obtaining ultrasound images of a patient, having a probe to be inserted into a body cavity of the patient and display means for displaying the ultrasound images, the probe comprising:

an insertion portion having a flexible tubular body;

a hollow housing provided at one end of the insertion portion;

a transducer mounted in said housing, said transducer having a flat surface and being rotatable about an axis perpendicular to said flat surface; and a mark visible from the exterior of the housing for indicating a direction of the transducer provided on a surface of the rotation portion.

16. The ultrasound apparatus according to claim 11, the mark being provided on the surface of the transducer.

17. The ultrasound diagnosing apparatus according to claim 9, the mark being printed on the surface of the transducer.

18. The ultrasound apparatus according to claim 8, the rotation portion further comprising a frame provided around the transducer, wherein the mark is provided on a surface of the frame.

19. The ultrasound diagnosis apparatus according to claim 15, wherein the probe further comprises a detection means for electrically detecting a rotation angle of the transducer and the display means displays the detected rotation angle, further comprising:

correction means for correcting the displayed rotation angle.

20. The ultrasound diagnosing apparatus according to claim 19, the correction means comprising input means for inputting correction data.

21. The ultrasound diagnosing apparatus according to claim 15, the housing further comprising a window being transparent such that the surface of the transducer can be viewed therethrough.

22. The ultrasound diagnosing apparatus according to claim 21, the window having a scale.

23. The ultrasound diagnosing apparatus according to claim 15, a part of the housing which is around the transducer having a scale.

24. The ultrasound diagnosis apparatus of claim 15, further comprising:

a motor disposed in the housing for rotating the transducer; and operation means for operating the motor, electrically connected to the motor and provided at the other end of the insertion portion.

25. The ultrasound diagnosis apparatus according to claim 24, further comprising detection means for electrically detecting a rotation angle of the transducer, being connected to the transducer.

26. The ultrasound diagnosis apparatus according to claim 25, the display means displaying the rotation angle detected by the detection means.

27. An ultrasound probe for insertion into a body cavity of a patient to obtain ultrasound images of the patient, comprising:

an insertion portion having a flexible tubular body;

a hollow housing provided at one end of the insertion portion; and an array of transducer elements, said array having a flat surface, for transmitting and receiving ultrasound waves in a plane perpendicular to the surface, wherein said array is provided in the housing and is rotatable around an axis perpendicular to the surface; and detection means for electrically detecting a rotation angle of the plane, being connected to the transducer in the housing.

28. The ultrasound probe according to claim 27, the detection means being connected to the transducer coaxially.

29. The ultrasound probe according to claim 27, the motor disposed parallel to the rotation axis of the transducer, being connected to the array of transducer elements with a gear therebetween.

30. An ultrasound diagnosis apparatus for obtaining ultrasound images of a patient, having a probe to be inserted into a body cavity of the patient and display means for displaying the ultrasound images, the probe comprising:

an insertion portion having a flexible tubular body;

a hollow housing provided at one end of the insertion portion;

an array of transducer elements, said array having a flat surface, for transmitting and receiving ultrasound waves in a plane perpendicular to the surface, wherein said array is provided in the housing, and is rotatable around an axis perpendicular to the surface; and detection means for electrically detecting a rotation angle of the plane, being connected to the transducer in the housing.

31. The ultrasound diagnosis apparatus according to claim 30, the detection means being connected to the transducer coaxially.

32. The ultrasound diagnosis apparatus according to claim 30, including a motor disposed parallel to the rotation axis of the transducer, being connected to the transducer with a gear therebetween.

33. The ultrasound diagnosis apparatus according to claim 30, the display means displaying the rotation angle detected by the detection means.

34. An ultrasound probe for insertion into a body cavity of a patient to obtain ultrasound images of the patient, comprising:

an insertion portion having a flexible tubular body;

a hollow housing provided at one end of the insertion portion;

a transducer rotatably provided in the housing;

a pulley coaxially connected to the transducer, being rotatable in connection with the transducer;

rotating means for rotating the pulley, having a string-like body;

operating means for operating the rotating means such that the transducer is rotated in a desired direction provided at the other end of the insertion portion; and slack removing means, provided to said rotating means, for removing a slack of the rotating means.

35. The ultrasound probe according to claim 34, further comprising detection means for electrically detecting a rotation angle of the transducer, provided between the transducer and the slack removing means.

36. The ultrasound probe according to claim 35, wherein the detection means is connected to the transducer coaxially.

37. The ultrasound probe according to claim 35, wherein:

the rotation means is wound around the pulley and both ends thereof are led to the operating means through the insertion potion; and in the vicinity of each of the both ends of the rotating means the detection means is mounted thereto.

38. The ultrasound probe according to claim 37, the two detection means are connected to control means for controlling the outputs of the detection means to be effective only when both of the detector means detect the rotation.

39. The ultrasound probe according to claim 34, the slack removing means having a cylinder in which the rotating means runs therethrough and is divided into two portions such that the two portions can move independently.

40. The ultrasound probe according to claim 34, the operating means comprising:

a drive pulley for driving the rotating means; and a knob for rotating the drive pulley.

41. The ultrasound probe according to claim 40, the operating means further comprising detection means for electrically detecting a rotation angle of the transducer which is represented by a distance of movement of the rotating means.

42. The ultrasound probe according to claim 34, wherein the rotation means is a wire.

43. The ultrasound probe according to claim 34, wherein the rotation means is a belt.

44. An ultrasound diagnosis apparatus for obtaining ultrasound images of a patient, having a probe to be inserted into a body cavity of the patient and display means for displaying the ultrasound images, the probe comprising:

an insertion portion having a flexible tubular body;

a hollow housing provided at one end of the insertion portion;

a transducer rotatably provided in the housing;

a pulley coaxially connected to the transducer, being rotatable in connection with the transducer;

rotating means for rotating the pulley, having a string-like body;

operating means for operating the rotating means such that the transducer is rotated in a desired direction provided at the other end of the insertion portion; and slack removing means, provided to said rotating means, for removing a slack of the rotating means.

45. The ultrasound diagnosis apparatus according to claim 44, further comprising detection means for electrically detecting a rotation angle of the transducer, provided between the transducer and the slack removing means.

46. The ultrasound diagnosis apparatus according to claim 45, the display means displaying the rotation angle detected by the detection means.

47. An ultrasound probe for insertion into a body cavity of a patient to obtain ultrasound images of the patient, comprising:

an insertion portion having a flexible tubular body;

a hollow housing provided at one end of the insertion portion;

an array of transducer elements, said array having a flat surface, for transmitting and receiving ultrasound waves in a plane perpendicular to the surface, wherein said array is provided in the housing, and is rotatable about an axis perpendicular to the surface;

a pulley coaxially connected to the transducer, being rotatable in connection with the transducer;

rotating means for rotating the pulley, having a string-like body;

operating means, provided at the other end of said insertion portion, for operating said rotating means such that said array is rotated in a desired direction; and indication means for indicating a rotation angle of the transducer.

48. The ultrasound probe according to claim 47, wherein the indication means comprising a rotation part rotated in connection with the rotating means.

49. The ultrasound probe according to claim 48, the rotation part constituting a rotation knob being mounted on the operating means.

50. The ultrasound probe according to claim 49, the insertion portion comprising an angle portion to be bent in a desired angle, the ultrasound probe further comprising:

angle wire means for bending the angle portion, being led to the operating means; and an angle knob for pulling the angle wire means, rotatably provided coaxially to the rotation knob.

51. The ultrasound probe according to claim 48, the rotation part having a mark on a surface thereof, the indication means further comprises a stationary part having a scale on a surface thereof.

52. The ultrasound probe according to claim 51, both of the rotation part and the stationary part having cylindrical shapes coaxially provided with different diameters.

53. The ultrasound probe according to claim 48, the rotation part having a scale on a surface thereof, the indication means further comprises a stationary part having a mark on a surface thereof.

54. The ultrasound probe according to claim 53, both of the rotation part and the stationary part having cylindrical shapes coaxially provided with different diameters.

55. An ultrasound diagnosis apparatus for obtaining ultrasound images of a patient, having a probe to be inserted into a body cavity of the patient and display means for displaying the ultrasound images, the probe comprising:

an insertion portion having a flexible tubular body;

a hollow housing provided at one end of the insertion portion;

a transducer elements rotatably provided in the housing;

an array of transducer elements, said array having a flat surface, for transmitting and receiving ultrasound waves in a plane perpendicular to the surface, wherein said array is provided in the housing and is rotatable about an axis perpendicular to the surface;

a pulley coaxially connected to the transducer, being rotatable in connection with the transducer;

rotating means for rotating the pulley, having a string-like body;

operating means, provided at the other end of said insertion portion, for operating said rotating means such that said array is rotated in a desired direction; and indication means for indicating a rotation angle of the transducer.

* * * * *